(12) United States Patent
Kim et al.

(10) Patent No.: US 7,008,786 B2
(45) Date of Patent: Mar. 7, 2006

(54) MICROORGANISM PRODUCING L-LYSINE AND PROCESSES FOR PRODUCING L-LYSINE USING THE SAME

(75) Inventors: Seong-Jun Kim, Kyunggi-do (KR); Kyung-Han Lee, Seoul (KR); Jin-Suck Sung, Kyunggi-do (KR); Sang-Jo Lim, Kyunggi-do (KR); Jae-Woo Jang, Kyunggi-do (KR)

(73) Assignee: Cheil Jedang Corporation, Seoul (KR)

( * ) Notice: Subject to any disclaimer, the term of this patent is extended or adjusted under 35 U.S.C. 154(b) by 478 days.

(21) Appl. No.: 10/204,906

(22) PCT Filed: Dec. 28, 2001

(86) PCT No.: PCT/KR01/02300

§ 371 (c)(1),
(2), (4) Date: Aug. 26, 2002

(87) PCT Pub. No.: WO02/053707

PCT Pub. Date: Jul. 11, 2002

(65) Prior Publication Data

US 2003/0124688 A1    Jul. 3, 2003

(30) Foreign Application Priority Data

Dec. 30, 2000  (KR) .............................. 2000-87097

(51) Int. Cl.
*C12N 1/20*    (2006.01)

(52) U.S. Cl. ................... 435/252.1; 424/93.4; 435/115
(58) Field of Classification Search ............ 435/252.1, 435/115; 424/93.4
See application file for complete search history.

(56) References Cited

U.S. PATENT DOCUMENTS

| | | | | |
|---|---|---|---|---|
| 3,687,810 A | * | 8/1972 | Kurihara et al. ............. | 435/115 |
| 3,929,571 A | * | 12/1975 | Kubota et al. .............. | 435/115 |
| 4,623,623 A | * | 11/1986 | Nakanishi et al. .......... | 435/115 |
| 5,268,293 A | | 12/1993 | Oh et al. | |
| 5,302,521 A | | 4/1994 | Nakano et al. | |

FOREIGN PATENT DOCUMENTS

JP    2234686    9/1990

OTHER PUBLICATIONS

Westley, John W. "Antibiotic Structure and Biosynthesis." *Journal of Natural Products*. vol. 49, No. 1, pp. 35-47. Jan.-Feb. 1986.

* cited by examiner

*Primary Examiner*—Irene Marx
(74) *Attorney, Agent, or Firm*—Nath & Associates; Viviana Amzel; Lee C. Heiman

(57) ABSTRACT

Disclosed are a Coryneform bacterium having resistance to an antibiotic, monensin, and producing L-lysine, and a process for producing L-lysine by a direct fermentation, which comprises culturing said microorganism in a fermentation medium, accumulating L-lysine in the resulting culture broth, and recovering L-lysine therefrom.

1 Claim, No Drawings

MICROORGANISM PRODUCING L-LYSINE AND PROCESSES FOR PRODUCING L-LYSINE USING THE SAME

TECHNICAL FIELD

The present invention relates to a microorganism producing L-lysine and to a process for producing L-lysine using the same. More specifically, the invention relates to *Corynebacterium glutamicum* CJM107 (KCCM-10227) having a resistance to an antibiotic, monensin, and having an ability to produce L-lysine in a high yield, and to the process for producing L-lysine by fermentation using the same.

BACKGROUND ART

L-lysine, one of essential amino acids, is widely used as animal feed, medicament, food, etc. A demand thereon has been recently increased according to a tendency to prevent environmental pollution by livestock wastewater through reinforcing a regulation on nitrogenous or phosphorous ingredients in livestock excretions. It is estimated that L-lysine as an additive to animal feed had a market scale of about five hundred thousands tons in 1999, and expected that a demand thereon will continuously rise by about an average of 10% every year. As described above, L-lysine is a large item in the fermentation product market. Therefore, it is expected that a big economic effect will be obtained by improving L-lysine productivity through development of a new L-lysine-producing strain or improving its fermentation process.

L-lysine has been heretofore produced using various auxotrophic strains, or drug-resistant or sensitive strains belonging to Coryneform bacteria. It has also been produced using an antibiotic-resistant strain, for example, bacitracin-resistant (Japanese Patent No. 1,765,413), sulfa drug-resistant (Korean Patent Laid-Open No. 81-1746) or iturin-resistant (Japanese Patent No. 2,578,413) strain, or a strain with resistance to two or more antibiotics, such as streptomycin and rifampicin (U.S. Pat. No. 4,623,623). However, a strain with resistance to an antibiotic, monensin, has never been reported.

DISCLOSURE OF THE INVENTION

The present inventors extensively studied processes for producing L-lysine by fermentation to produce L-lysine in the industrial scale and economical manner. As a result, the inventors found that the productivity of L-lysine could be improved by providing a Coryneform bacterium producing L-lysine resistant to monensin.

Monensin is an antibiotic produced from *Streptomyces* spp., one of *Actinomycetes*. It is known to affect functions of bacterial cell membrane and proton motive force (Journal of Natural Product, 49, 35–47, 1986). Specifically, monensin acting as an ionophore changes bacterial cell membrane and proton motive force thereby changing physiological properties of bacteria.

For the efficient production of L-lysine that L-lysine, biosynthesized within cells, should be well secreted to the outside of cells by a membranous protein, L-lysine exporter. Membrane potential formed across the cell membrane by proton motive force is known to be involved in extracellular secretion of L-lysine by its exporter (Eur. J. Biochem, 220, 137–143, 1991). From the reaction mechanism of monensin, the present inventors could improve the productivity of L-lysine by providing a Coryneform bacterium with resistance to monensin.

In the present invention, a Coryneform bacterium includes any microorganism belonging to the genus of *Corynebacterium* or *Brevibacterium*. In the present invention, any strain can be used as a parent strain, as long as it has an ability to produce L-lysine and belongs to a Coryneform bacterium. One specific example thereof is *Corynebacterium glutamicum* CH77.

Hereinafter, the present invention will be explained in more detail.

A monensin-resistant strain can be obtained by treating a parent strain of $10^7$–$10^8$/ml with a chemical mutagen, N-methyl-N'-nitro-N-nitrosoguanidine, of a final concentration of 500 $\mu$g/ml at 30° C. for 30 minutes and isolating a strain that grows in a minimal agar plate medium containing a concentration of monensin, which does not permit the growth of the parent strain. The mutant strain of the present invention can be obtained by further culturing the obtained monensin-resistant strain, evaluating its ability to produce L-lysine, and selecting a strain having an improved ability to produce L-lysine.

The parent strain and the monensin-resistant strain derived therefrom as described above have the following characteristics:

Parent strain: *Corynebacterium glutamicum* CH77 (KFCC10881) which is S-(2-aminoethyl)cystein-resistant, aminohydroxyvaleric acid-resistant, methyllysine-resistant, sodium azide-resistant, homoserine-leaky and leucine-requiring.

Mutant strain: *Corynebacterium glutamicum* CJM107 (KCCM-10227) which is S-(2-aminoethyl)cystein-resistant, aminohydroxyvaleric acid-resistant, methyllysine-resistant, sodium azide-resistant, homoserine-leaky and leucine-requiring, and further, monensin-resistant.

The monensin-resistant strain, *Corynebacterium glutamicum* CJM107, was deposited under the Budapest Treaty to the Korean Culture Center of Microorganisms (KCCM) of 361-21, Yurim B/D, Hongje-1-dong, Seodaemun-gu, Seoul 102-091, Republic of Korea, on Nov. 15, 2000, with the Accession No. KCCM-10227.

The parent CH77 strain and the mutant CJM107 strain were tested for their resistance to monensin by the following method. Cells were grown in a Luria-Bertani (LB) liquid medium for 16 hours. Then, the cells were washed twice with a sterilized physiological saline and then, appropriately diluted and cultivated on a minimal agar plate medium [glucose 10 g, $(NH_4)_2SO_4$ 2 g, urea 2 g, $KH_2PO_4$ 1 g, $K_2HPO_4$ 3 g, $MgSO_4.7H_2O$ 0.5 g, $FeSO_4.7H_2O$ 10 mg, $MnSO_4.7H_2O$ 10 mg, biotin 100 $\mu$g, Thiamin.HCl 100 $\mu$g, $CaCl_2.2H_2O$ 100 $\mu$g, $Na_2B_4O_7.10H_2O$ 80 $\mu$g, $(NH_4)_6Mo_7O_{24}.4H_2O$ 40 $\mu$g, $ZnSO_4.7H_2O$ 10 $\mu$g, $CuSO_4.7H2O$ 10 $\mu$g, $MnCl_2.4H_2O$ 10 $\mu$g, $FeCl_3.6H_2O$ 1 mg, agar 20 g, if necessary L-leucine 0.1 g, if necessary L-threonine 0.1 g, if necessary L-methionine 0.1 g, per distilled water of 1l (pH 7.0)] containing monensin of 7,000 $\mu$g/l for 4 days. The growth of each strain is shown in the following Table 1.

TABLE 1

Resistance to monensin of *Corynebacterium glutamicum* CH77 and CJM107

| Monensin (g/l) | CH77 | CJM107 |
| --- | --- | --- |
| 0 | +++ | +++ |
| 7,000 | − | +++ |

+++: Sufficient growth, −: No growth

A medium conventionally used for amino acid fermentation can be used for culturing microorganisms used in the present invention. That is, any medium can be used in the present invention, as long as it contains carbon sources, nitrogen sources, inorganic salts, growth factors, etc., which are assimilable by the strain used. Carbohydrates, such as molasses, sucrose, glucose, fructose, etc., may be used as carbon sources. Inorganic nitrogen sources, such as ammonia, ammonium sulfate, urea, ammonium chloride, etc., and organic nitrogen sources, such as yeast extracts, yeast hydrolysates, soybean meal acid hydrolysates, peptone, corn steep liquor, etc., may be used as nitrogen sources. Potassium dihydrogen phosphate, dipotassium hydrogen phosphate, magnesium sulfate, sodium chloride, ferrous sulfate, manganese sulfate, calcium carbonate, etc., may be used as inorganic compounds. In addition, if necessary, vitamins, such as biotin and thiamin, and amino acids, such as leucine, homoserine, methionine, threonine, etc., can be used.

Cultivation is carried out under aerobic condition, for example, by shaking culture or aeration agitation submerged culture, at 25 to 35° C. The pH of the medium is in the range of 6 to 8, and is preferably maintained at around neutrality. The pH can be adjusted with calcium carbonate, urea or ammonia. Usually, after culturing for 1 to 7 days, L-lysine is formed and accumulated in the resulting culture broth. After completion of culturing, the culture broth is treated with sulfuric acid or hydrochloric acid, and then, L-lysine can be recovered from the culture broth by use of ion-exchange resin treatment, concentration, salting-out, and isoelectric focusing combination.

BEST MODE FOR CARRYING OUT THE INVENTION

This invention will be specifically explained by the following examples.

EXAMPLE 1

*Corynebacterium glutamicum* CH77 and CJM107 were inoculated in a 250 ml corner-baffled flask containing 25 ml of the following seed medium and cultured with shaking (220 rpm) at 30° C. for 20 hours. To a 250 ml corner-baffled flask containing 25 ml of the following production medium was inoculated 1 ml of the seed medium and cultured while shaking (220 rpm) at 32° C. for 96 hours. After completion of culturing, the amount of L-lysine was measured by HPLC. L-lysine as L-lysine-HCl in the culture liquor of *Corynebacterium glutamicum* CH77 and CJM107 was 47 g/l and 51 g/l, respectively.

Seed Medium (pH 7.0)

Raw sugar 50 g, Peptone 10 g, yeast extract 10 g, urea 5 g, $KH_2PO_4$ 4 g, $K_2HPO_4$ 8 g $MgSO4.7H_2O$ 0.5 g, biotin 100 μg and thiamin.HCl 1000 μg (per 1 liter of process water)

Production Medium (pH 7.0)

Molasses or pretreated molasses (as reducing sugar) 50 g, raw sugar 50 g, yeast extract 4 g, $(NH_4)_2SO_4$ 40 g, urea 4 g, $KH_2PO_4$ 1 g, NaCl 2.5 g, $MgSO_4.7H_2O$ 1 g, $FeSO_4.7H2O$ 10 mg, $MnSO_4.5H_2O$ 10 mg, biotin 100 μg, thiamin hydrochloride 200 μg, $CaCO_3$ 40 g, if necessary L-leucine 0.4 g, if necessary L-threonine 0.1 g, if necessary L-methionine 0.1 g (per 1 liter of process water)

EXAMPLE 2

The CJM107 strain was cultivated in the medium containing molasses and raw sugar. After cultivation, sulfuric acid or hydrochloric acid was added to the L-lysine fermentation broth of 1 liter to adjust the pH to 2.0 thereby converting $Ca^{2+}$ ions to $CaSO_4$ or $CaCl_2$. Then, the broth applied to be adsorbed upstream onto a cation exchange resin (Dianion SK-1B, SK-1BL) regenerated in ammonium ion form. Subsequently, it was washed with desalted water to remove cell mass remaining in the resin layer, and then, the concentrated fraction of L-lysine was recovered therefrom by eluting with 2 N ammonium hydroxide. After concentration of the recovered fraction, the concentrate was adjusted to the pH 5.0 and cooled down to 20° C. thereby to form crystals of L-lysine.

Slurries obtained after the completion of crystallization were centrifuged to obtain the first wet product. The mother liquor was concentrated again by a batch process and crystallized to obtain the second wet product. The first and second wet products were combined and dried to obtain a dry product of 46 g containing 98.5% of L-lysine.

EXAMPLE 3

The CJM107 strain was cultivated in the medium containing pretreated molasses and raw sugar. After cultivation, sulfuric acid was added to the L-lysine fermentation broth of 1 liter to adjust the pH to 2.0 thereby converting $Ca^{2+}$ ions to $CaSO_4$ Then, the broth applied to be adsorbed upstream onto a cation exchange resin (Dianion SK-1B, SK-1BL) regenerated in ammonium ion form. Subsequently, it was washed with desalted water to remove cell mass remaining in the resin layer, and then, the concentrated fraction of L-lysine was recovered therefrom by eluting with 2 N ammonium hydroxide. After concentration of the recovered fraction, the concentrate was adjusted to the pH 5.0 and cooled down to 20° C. thereby to form crystals of L-lysine Slurries obtained after the completion of crystallization were centrifuged to obtain the first wet product. The mother liquor was concentrated again by a batch process and crystallized to obtain the second wet product. The first and second wet products were combined and dried to obtain a dry product of 47 g containing 99% of L-lysine.

INDUSTRIAL APPLICABILITY

According to the present invention, the fermentation concentration and the yield of L-lysine could be improved by making a Coryneform bacterium producing L-lysine resistant to monensin by an artificial mutation thereof. Therefore, the Coryneform bacterium having resistance to monensin and having the ability to produce L-lysine is very useful for L-lysine production.

What is claimed is:

1. An isolated, purified *Corynebacterium glutamicum* CJM107 deposited as KCCM-10227, having resistance to monensin and producing L-lysine.

* * * * *